United States Patent [19]

Faas

[11] Patent Number: 5,355,561
[45] Date of Patent: Oct. 18, 1994

[54] METHOD AND APPARATUS FOR MEASURING A CHARACTERISTIC OF A FIBER STRUCTURE, SUCH AS A FIBER COMPOSITE OR A SLIVER

[75] Inventor: Jurg Faas, Dinhard, Switzerland

[73] Assignee: Maschinenfabrik Rieter AG, Winterthur, Switzerland

[21] Appl. No.: 785,064

[22] Filed: Oct. 30, 1991

[30] Foreign Application Priority Data

Nov. 2, 1990 [CH] Switzerland .............. 3 496/90-0

[51] Int. Cl.⁵ .................. D01G 21/00; G01N 21/00; G01N 21/86; G01J 3/50
[52] U.S. Cl. .................. 19/300; 250/226; 250/571; 356/429; 19/145.5
[58] Field of Search .............. 19/300, 145.5, 65 A, 19/239, 150, 157; 250/339, 341, 571; 356/238, 429, 432, 425, 446, 430; 73/866

[56] References Cited

U.S. PATENT DOCUMENTS

| | | | |
|---|---|---|---|
| 3,471,702 | 10/1969 | Van Veld | 19/239 |
| 3,524,988 | 8/1970 | Gaither, IV | 356/238 |
| 3,573,476 | 4/1971 | Falcoff et al. | 356/425 |
| 3,925,850 | 12/1975 | Lytton | 19/150 X |
| 3,986,778 | 10/1976 | Mathisen et al. | 356/244 |
| 4,022,534 | 5/1977 | Kishner | 356/446 |
| 4,284,356 | 8/1981 | Heilman | 356/429 |
| 4,288,160 | 9/1981 | Lodzinski | 356/429 X |
| 4,306,450 | 12/1981 | Moser | 19/239 X |
| 4,490,618 | 12/1984 | Cielo | 356/429 X |
| 4,758,968 | 7/1988 | Lord . | |
| 4,766,647 | 8/1988 | Ackermann, Jr. et al. . | |
| 4,786,817 | 11/1988 | Boissevain et al. | 356/429 X |
| 4,845,730 | 7/1989 | Mercer | 250/339 X |
| 4,963,757 | 10/1990 | Liefde et al. | 356/429 X |
| 4,982,477 | 1/1991 | Hösel | 19/239 X |
| 4,990,793 | 2/1991 | Bönigk et al. | 356/238 X |
| 5,007,136 | 4/1991 | Artzt et al. | 19/65 A |
| 5,025,533 | 6/1991 | Faas et al. | 19/145.5 |
| 5,054,317 | 10/1991 | Laubscher | 356/238 X |
| 5,159,189 | 10/1992 | Anderegg et al. | 356/429 X |
| 5,194,911 | 3/1993 | Stutz | 356/429 X |

FOREIGN PATENT DOCUMENTS

| | | | |
|---|---|---|---|
| 0399315 | 11/1990 | European Pat. Off. | 19/65 A |
| 1931929 | 2/1979 | Fed. Rep. of Germany . | |
| 3204146 | 8/1983 | Fed. Rep. of Germany | 356/432 |
| 3327966 | 2/1985 | Fed. Rep. of Germany . | |
| 0277331 | 3/1990 | Fed. Rep. of Germany | 250/339 |
| 0362538 | 4/1990 | Fed. Rep. of Germany . | |
| 0032153 | 2/1989 | Japan | 250/341 |
| 0094248 | 4/1989 | Japan | 250/339 |
| 2044443 | 10/1980 | United Kingdom | 250/339 |
| 2172102 | 9/1986 | United Kingdom | 250/341 |
| 2210907 | 6/1989 | United Kingdom . | |

OTHER PUBLICATIONS

Photothermal Methods of Optical Characterization of Materials, Murphy and Wetsel, Materials Evaluation, 44, Sep. 1986, 1224–1230.

Primary Examiner—Clifford D. Crowder
Assistant Examiner—John J. Calvert
Attorney, Agent, or Firm—Sandler Greenblum & Bernstein

[57] ABSTRACT

To ensure that on-line measurements performed at a moving or stationary fiber structure, such as a fiber composite or a sliver, deliver useful and reproducible measuring values, the fiber structure, whether such be fiber composites or fiber slivers, must be compressed at the location where they pass a measuring location or site where there is accomplished the measurement with a commercially available measuring instrument or apparatus. According to the invention, there is selected as the measuring location or site a location of the fiber processing process where the fiber structure is compressed any way by virtue of the undergoing fiber processing process.

25 Claims, 5 Drawing Sheets

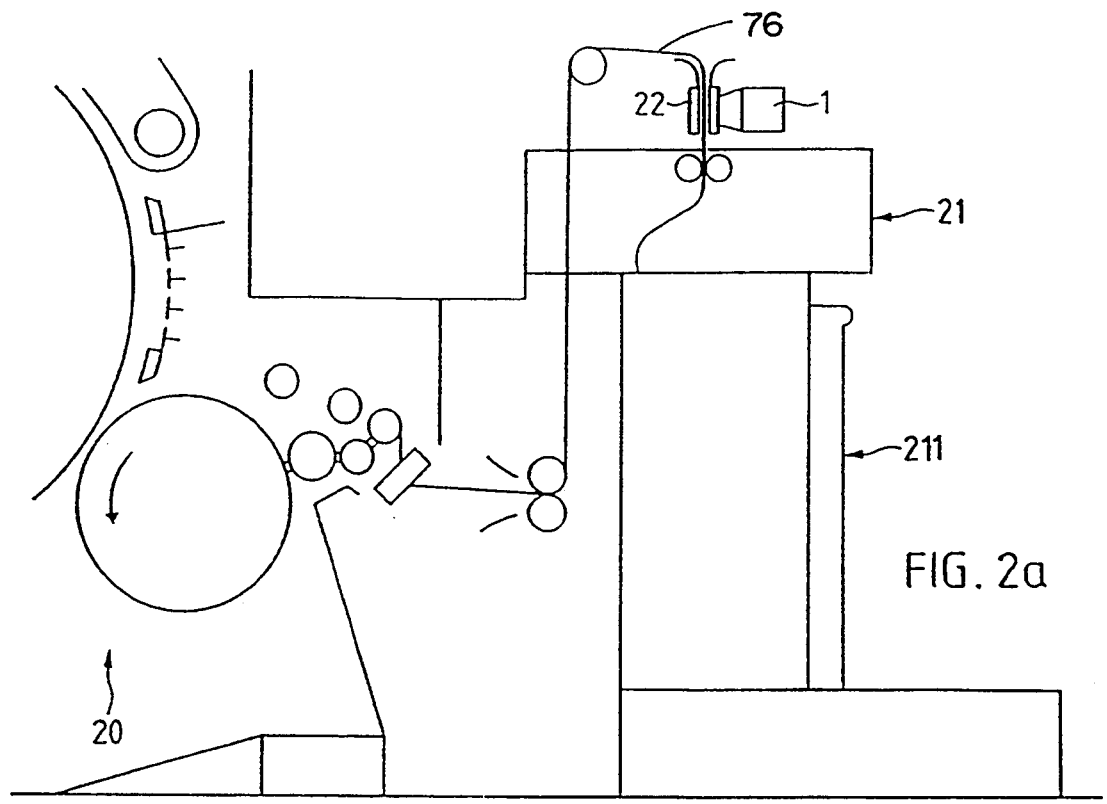
FIG. 2a
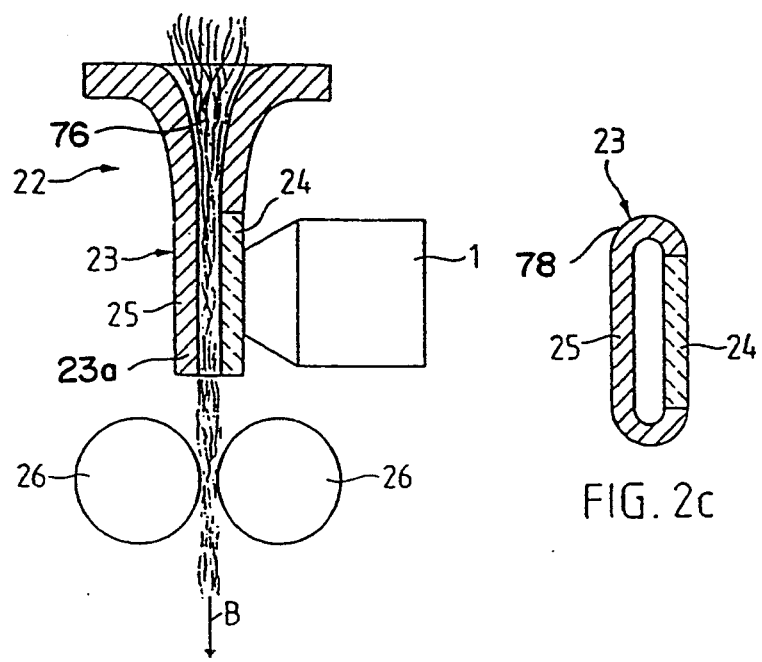
FIG. 2b
FIG. 2c

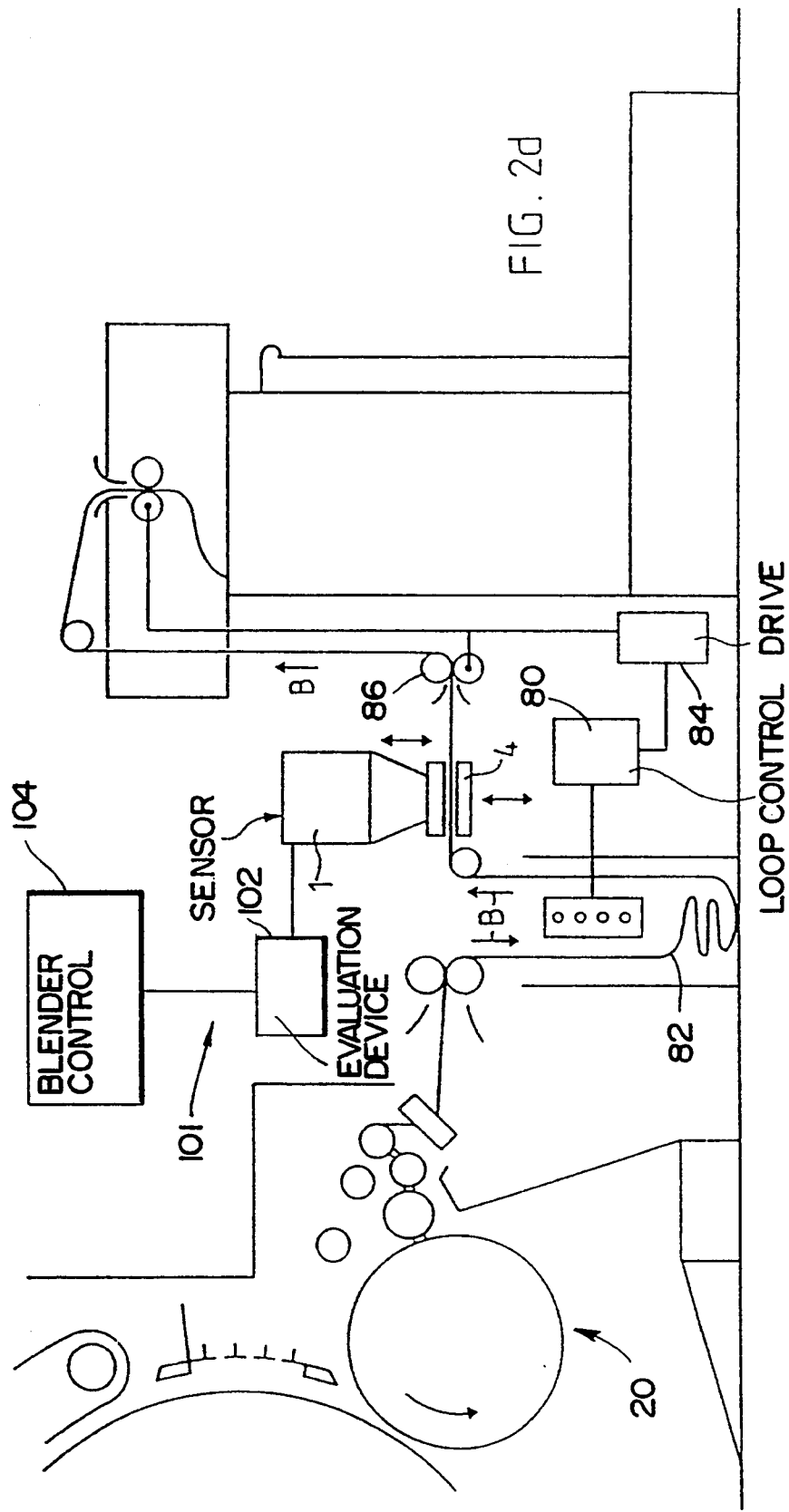

METHOD AND APPARATUS FOR MEASURING A CHARACTERISTIC OF A FIBER STRUCTURE, SUCH AS A FIBER COMPOSITE OR A SLIVER

BACKGROUND OF THE INVENTION

1. Field of the Invention

The present invention relates to a new and improved method and apparatus for measuring a characteristic or property of a fiber structure, such as a fiber composite or a sliver. The term "fiber composite", as used herein, is intended to mean an agglomeration or accumulation of fibers.

The present invention also relates to an improved method of blending or mixing textile fibers of different origin.

2. Discussion of the Background and Material Information

The commonly assigned European Published Patent Application No. 0,362,538, published Apr. 11, 1990 and the cognate U.S. Pat. No. 5,025,533, granted Jun. 25, 1991, teach a method of blending textile fibers of different origin or derivation in which each textile fiber origin possesses pregiven or predetermined fiber properties or characteristics and in which each textile fiber origin constitutes a mixed or blended component of a predetermined percentual proportion. Further, the entire fiber mixture exhibits pregiven or predetermined fiber characteristics or properties and the mixed components are variable components which can be controlled at all times. In order to attain the aforementioned fiber characteristics or properties of the fiber mixture, the percentual proportion of each component is automatically optimized while taking into account the fiber properties of the individual components, in that the component mixture or blend is determined as a function of pregiven and determined properties of an intermediate product which is subsequently manufactured, preferably a card sliver or a subsequently manufactured final or end product, preferably a yarn. Upon deviation of the component mixture or blend from the pregiven and determined properties such deviation is automatically corrected without delay.

The disclosed and illustrated method of the aforementioned commonly assigned European Published Patent Application No. 0,362,538, published Apr. 11, 1990 and the cognate U.S. Pat. No. 5,025,533, granted Jun. 25, 1991, teach the possibility of transferring textile fibers of different origin either directly from the fiber bales or from component cells or bins to a mixer or blender where there occurs homogeneous mixing or blending of such components. The resultant product of the mixer or blender is subsequently cleaned in a blowing room or "cleaning station", and thereafter transferred for processing to a card or carding machine. After the card the card sliver is checked in a color checking or testing apparatus and an appropriate signal is delivered to a control which controls the component mixing operation.

In the context of this disclosure, the term "origin", or equivalent expressions, embrace cotton fiber bales or fiber bales containing synthetic or man-made fibers, so that during the mixing or blending there can come under consideration mixtures composed of different types of cotton or a mixture of cotton fibers and synthetic fibers.

In this connection there exists the requirement of being able to determine the proportion of synthetic fibers present in a fiber mixture or blend. Previously, this determination was made by laboratory chemical analysis of individual samples, the performance of which required a considerable amount of time.

SUMMARY OF THE INVENTION

Therefore, with the foregoing in mind, it is a primary object of the present invention to provide an improved method and apparatus for determining a characteristic or property of a fiber structure, such as a fiber composite or a sliver in a manner which is not afflicted with the afore-discussed limitations and drawbacks of the prior art.

Another and more specific object of the present invention aims at providing an improved method and apparatus for enabling accurate and quick determination of the mixing or blending of different types of fibers, especially the concentration or proportion of synthetic fibers in the entire fiber mixture or blend.

Still a further noteworthy object of the present invention is the provision of an improved method and apparatus for enabling accurate and quick determination of the mixing or blending of different types of fibers, especially the concentration or proportion of synthetic fibers in the entire fiber mixture or blend, in an on-line mode during processing of the textile fibers.

Another significant object of the present invention is concerned with an improved method of controllably blending or mixing textile fibers of different origin in a highly accurate, reliable and efficient manner.

Now in order to implement these and still further objects of the present invention, which will become more readily apparent as the description proceeds, the inventive method for enabling determination of the mixing or blending of different types of fibers, especially the concentration or proportion of synthetic fibers in the entire fiber mixture or blend is manifested, among other things, by the features that the determined characteristic or property of the fiber structure, such as that of an intermediate product, but also a final or end product, constitutes the concentration of individual pregiven or predetermined types of fibers contained in the entirety of the mixture, and there is measured such concentration.

The measurement of the concentration of individual pregiven or predetermined types of fibers contained in the entirety of the mixture is accomplished by evaluating spectrums in the near infrared range (by ultra-violet or fluorescence).

This is advantageously accomplished by carrying out the measurement such that there is illuminated or irradiated with radiant energy a travelling textile product, such as an intermediate product at a predetermined site or location of the fabrication process where there occurs compaction of the intermediate product by condensing or compression of such intermediate product. At the measurement site there is arranged a light passage for a measuring sensor in such a manner that the fabrication process is not hampered. The light passage receives light or radiant energy reflected back by the textile product which then impinges upon the measuring sensor, in particular light or radiant energy which is reflected back to the light passage in a direction substantially perpendicular to the lengthwise axis of the textile product and, when moving, substantially perpendicular to its direction of travel, and such reflected light can be evaluated. As the measurement site there can be selected a location of the fiber processing process where the fiber structure, for example, a fiber sliver is deposited or coiled in overlapping layers or convolutions.

The compaction of the fiber structure at the measuring or measurement location or site can be accomplished by gathering together or compressing the fiber structure at the measuring location or site.

As indicated previously, the present invention also is concerned with an apparatus for determining a characteristic of a fiber structure constituting the concentration of individual pregiven types of fibers in the entire fiber structure. This apparatus comprises means for exposing the fiber structure to a fiber processing process, and means for compacting the fiber structure at a measuring location containing a light passage arranged such that there is not affected the fiber processing process during such time that the fiber structure is exposed to the fiber processing process. Still further, such apparatus comprises means for measuring the concentration of the individual pregiven types of fibers in the fiber composite, by illuminating or irradiating the fiber structure with light transmitted through the light passage at the measuring location where the fiber structure is compacted, this measuring means receiving light reflected back from the fiber structure in a direction substantially perpendicular to the lengthwise axis of the fiber structure, and such measuring means including means for evaluating the received light.

According to the invention, the measuring means advantageously comprise spectrometer means. Such spectrometer means can be a FT-NIR-spectrometer of Bühler Ltd., located at Utzwil, Switzerland.

As to a further aspect of the apparatus, the means for compacting the fiber structure at the measuring location comprises a sliver funnel which includes an opening defining the measuring opening, and such measuring opening possesses a substantially flat rectangular cross-sectional configuration. Furthermore, the measuring means comprises a measuring sensor positioned substantially perpendicular to the neck of the sliver funnel which has a transparent wall which confronts the measuring sensor. The opposite wall of the sliver funnel need not possess any particular properties in terms of the performed measurement.

It is contemplated, according to a possible construction, that the means for compacting the fiber structure at the measuring location comprises at least one respective transport belt arranged to opposite sides of the fiber structure which may define or constitute a moving fiber structure. A transparent plate is arranged at one side of the moving fiber structure. The measuring sensor is arranged at a side or face of the transparent plate which faces away from the moving fiber structure, and the transport belts and the transparent plate are arranged such that, as viewed in a predetermined direction of travel of the moving fiber structure, the spacing between at least one of the transport belts and the transparent plate successively decreases in the direction of the transparent plate and assumes a minimum value at the region of the transparent plate.

Still further, the at least one respective transport belt arranged to opposite sides of the moving fiber structure can comprise two transport belts arranged at the side of the moving fiber structure which confronts the measuring sensor and a further transport belt arranged at the other side of the moving fiber structure which faces away from the measuring sensor. The transparent plate is arranged between the two transport belts arranged at the side of the moving fiber structure which confronts the measuring sensor and respectively define an infeed transport belt and an outfeed transport belt. Moreover, there are desirably provided substantially plate-shaped brackets for guiding the infeed transport belt and the outfeed transport belt to the immediate region of the transparent plate.

Certain of the more notable advantages of the present invention reside in the fact that at an incipient stage of the fiber processing process there can be determined the mixture or blend of natural and synthetic fibers with sufficiently great accuracy. This is particularly of advantage in consideration of the appreciably different price of synthetic fibers in comparison to natural fibers, which explains why different countries prescribe by law exactly the amount of synthetic fibers which can be contained in a textile product. Therefore, the present invention also can be beneficially employed in conjunction with the method of the earlier mentioned, commonly assigned European Published Patent Application No. 0,362,538, published Apr. 11, 1990 and its cognate U.S. Pat. No. 5,025,533, granted Jun. 25, 1991, to which reference may be readily had and the disclosures of which are incorporated in their entirety herein by reference.

To that end it is contemplated that in a method of blending textile fibers of different fiber origin, wherein each fiber origin possesses pregiven fiber characteristics and in which each fiber origin constitutes a mixing component of a pregiven or predetermined percentual proportion, and wherein the entire fiber mixture possesses pregiven or predetermined fiber characteristics, and the mixing components constitute variable components which can be controlled at all times, and the percentual proportion of each component, in order to attain such predetermined fiber characteristics of the entire fiber mixture, is automatically optimized while taking into account the fiber characteristics of the individual components, and the component mixture is determined as a function of pregiven and determined characteristics of a product which is subsequently fabricated, and upon deviation from such pregiven and determined characteristics of the product such deviations are immediately and automatically corrected, there are performed the steps of selecting as the characteristic of a fiber structure which is to be determined and defining the product, the concentration of individual pregiven types of fibers in the entire fiber structure, and measuring the concentration of the individual pregiven types of fibers in the entire fiber structure.

BRIEF DESCRIPTION OF THE DRAWINGS

The invention will be better understood and objects other than those set forth above, will become apparent when consideration is given to the following detailed description thereof. Such description makes reference to the annexed drawings wherein:

FIG. 2a schematically depicts an exemplary embodiment of apparatus according to the present invention for performing the inventive method which employs the process-dictated technique of compression of the fiber structure, such as here a sliver;

FIG. 2b schematically illustrates, somewhat on an enlarged scale, a portion of the arrangement of FIG. 2a and, in particular, the funnel or trumpet structure thereof, and which is used for investigating that characteristic or property of the fiber structure which it is desired to determine;

FIG. 2c schematically illustrates a sectional detail of the funnel or trumpet structure depicted in the arrangement of FIG. 2b;

FIG. 2d schematically illustrates a somewhat different apparatus embodiment from that shown in FIG. 2a in conjunction with loop control means, evaluation means and a blender control means;

FIG. 3b is a top plan view of the apparatus depicted in FIG. 3a;

FIG. 5b schematically depicts a fragmentary sectional detail view of the arrangement of FIG. 5a.

DETAILED DESCRIPTION OF THE PREFERRED EMBODIMENTS

Figure 1A:
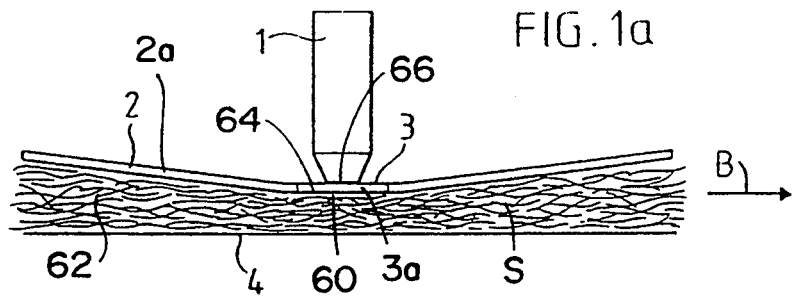
FIG. 1a schematically illustrates a general possible construction of apparatus which can be used in the method according to the present invention.
Figure 1B:
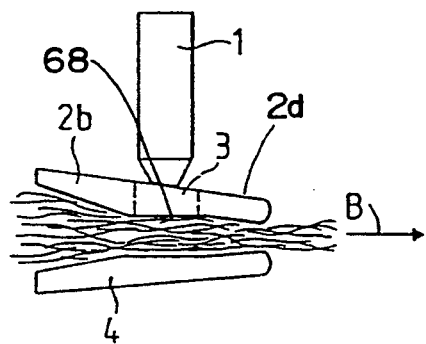
FIG. 1b schematically illustrates a first possible construction of apparatus for the practice of a first possible method according to the present invention.

Describing now the drawings, it is to be understood that only enough of the construction of the apparatus for determining a characteristic or property of a fiber structure, such as a fiber composite or a sliver, has been depicted therein, in order to simplify the illustration, as needed for those skilled in the art to readily understand the underlying principles and concepts of the present invention.

Turning attention now initially to FIG. 1, there is depicted a measuring or measurement sensor or probe 1 which is arranged substantially perpendicular to the direction of travel indicated by the arrow B of the fiber structure S to be investigated, such as a fiber composite or a sliver, a particular characteristic or property of which is to be determined, such as the concentration or proportion of the blend of natural and synthetic fibers contained therein. The fiber structure S bears upon a support element 4 constituting part of a fiber structure compressing means 2. The upper surface 60 of this fiber structure S is located at a substantially constant spacing from the measuring sensor 1 as such fiber structure S moves therepast. At this point it is remarked that the measurement operation also could be carried out at a stationary fiber structure.

Let it be here assumed for purposes of discussion that this fiber structure S is a sliver 62 (although it also could be a fiber composite), then before such sliver 62 moves past a measuring location or site 64 where there is located the measuring sensor 1 for determining color values of the sliver 62, this sliver 62 is slightly compressed by the action of the compressing structure or means 2 which may be constituted by a compressing element or plate 2a and the confronting support or compressing element 4. The measurement operation can be performed through an appropriately transparent apparatus component 3, for instance, a plane glass plate or disk 3a, or else through a small opening extending through such compressing element 2a, in which case there can be omitted the use of the plane glass plate or disk 3a. By appropriately constructing the compressing structure or means 2, whether such be dictated by the nature of the fiber processing process or purely by virtue of measurement considerations, there is ensured that at the measuring location or site 64 the sliver 62 possesses a sufficient width in order to cover the entire measuring opening 66 of the measuring sensor 1.

Three different variants of the method for the compression of the sliver 62 are available at the region of the measuring site or location 64. According to the first variant depicted in FIG. 1b, the measurement operation is performed at a process location 68 defining the measuring site, where, as governed by the specifically undertaken fiber processing process, the sliver 62 is compressed, in other words, at the location where the compressing structure or means 2b, here a funnel or trumpet 2d constitutes an apparatus element which is inherent to or used anyway for that particular fiber processing process.

Figure 1C:
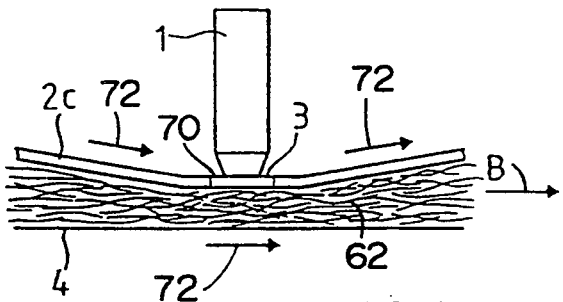
FIG. 1c schematically illustrates a second possible construction of apparatus for the practice of a second possible method according to the present invention.

According to the second variant depicted in FIG. 1c, the measuring operation is accomplished at any desired process location, such as the measuring location or site 70, and the moving or travelling sliver 62 is compressed at the region of this measuring location or site 70, without being braked, between the compressing means 2c containing the confronting support or compressing element 4 which travel along with the moving sliver 62 in the direction of the arrows 72.

Figure 1D:
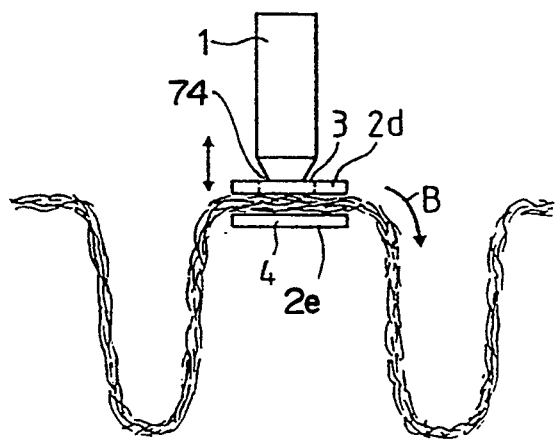
FIG. 1d schematically illustrates a third possible construction of apparatus for the practice of a third possible method according to the present invention.

With regard to the third variant shown in FIG. 1d, the measurement operation is performed at a process location or site 74, again defining a measurement site or location, where the sliver 62 loosely hangs through in loops (the loops being equatable to storages), so that for the measurement the movement of the sliver 62 is briefly interrupted and the sliver is compressed between the stationary compressing elements or plates 2d and 4 of the compressing structure or means 2e.

FIGS. 2a, 2b and 2c illustrate in greater detail an exemplary embodiment of measuring apparatus constructed according to the present invention and used in conjunction with a fiber processing machine or structure, here a conventional card or carding machine 20. In order to compress the sliver 76 there is exploited the compression of such sliver 76 which arises anyway by virtue of the use of a funnel or trumpet 22 or equivalent structure arranged at the outlet side of the card 20, in other words, there is made use of the technique considered previously with respect to the description of FIG. 1b. The details of the card 20 need not be here considered since they are totally unimportant for the understanding of the present invention. In particular and as schematically shown in FIG. 2a, this funnel or trumpet 22—also termed a condenser—can be part of a sliver depositing apparatus 21, like a sliver coiler apparatus or coiler as such is commonly used for the deposition or coiling of card slivers into sliver cans or containers 211. However, the funnel or trumpet 22 also may constitute the infeed funnel or trumpet for a stepped pair of rolls or may constitute the measuring funnel or trumpet which is used for measuring the density of the sliver.

Still further, and as touched upon previously, this FIG. 2a schematically shows, by way of example as a localization of the inventive apparatus, the departure of the sliver 76 from the card 20 and its delivery to the sliver depositing apparatus 21, here the exemplary depicted sliver coiler apparatus arranged at the sliver can or container 211. The measuring sensor 1 is mounted at the funnel or trumpet 22 of the sliver depositing or coiler apparatus 21. As particularly evident from FIG. 2b, for this purpose the funnel or trumpet 22 has a special construction. To that end, a neck or throat 23 of the funnel or trumpet 22 is constructed as a measuring tube or cuvette 23a. To ensure that the through-passing sliver 76 possesses a width which is adequate for the performance of the measurement operation, the neck 23 of the funnel or trumpet 22 advantageously possesses the cross-sectional configuration depicted in FIG. 2c which is in the form of a very flat quadrangle or rectangle having rounded corners 78. The wide side or wall 24 of the funnel neck 23 which confronts the measuring sensor 1 consists of any suitable transparent material. The oppositely situated wall 25 does not possess any special or particular properties in terms of the measurement operation. A pair of transport rolls or rollers 26 are arranged downstream of the funnel or trumpet 22 in the direction of extent of the funnel walls 24 and 25 and from which emerges the compressed sliver moving in the direction of the arrow B.

FIG. 2d depicts a modified arrangement in contrast to that shown in FIG. 2a, while following the principles considered with reference to FIG. 1d. There will be seen a control means or control 80 for the control of the loop formation or loop 82, which, for example, is disclosed in German Patent No. 1,931,929, published Feb. 11, 1971 and in that design likewise requires a start-stop mode of operation of the can filling during the measurement. This control means 80 controls a drive 84 for the rolls 86 located at the outlet side or downstream of the measuring sensor 1. Furthermore, the measuring sensor 1 is part of a measuring means, generally indicated by reference numeral 101, which includes a suitable evaluation device or means 102 for evaluating the measuring signals received from the measuring sensor 1. The evaluation device or means 102 is operatively connected with a control or control means 104 for controlling, for instance, blending of fiber constituents in the manner disclosed in the prior mentioned, commonly assigned European Published Patent Application No. 0,362,538, published Apr. 11, 1990 and its cognate U.S. Pat. No. 5,025,533, granted Jun. 25, 1991. Moreover, the described measurement can be accomplished, for example, through the use of a measuring means or apparatus of the well known Swiss firm Bühler Ltd., located at Uzwil, Switzerland, known as the "Bühler FT-NIR-Spectrometer".

Figure 3A:
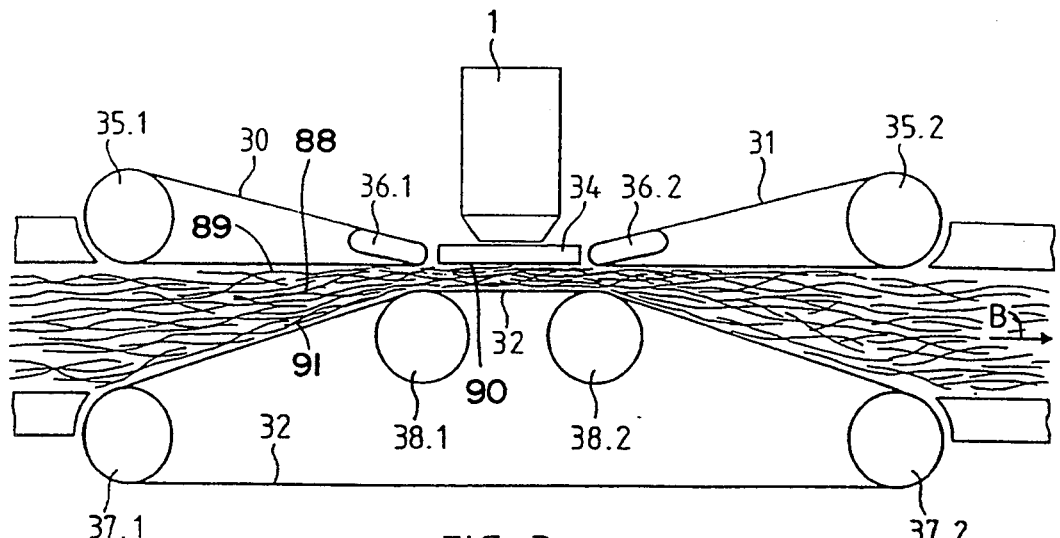
FIG. 3a is a fragmentary schematic elevational view of a further embodiment of apparatus for practicing the inventive method and equipped with structure for accomplishing sliver compression for performing the inventive method.
Figure 3B:
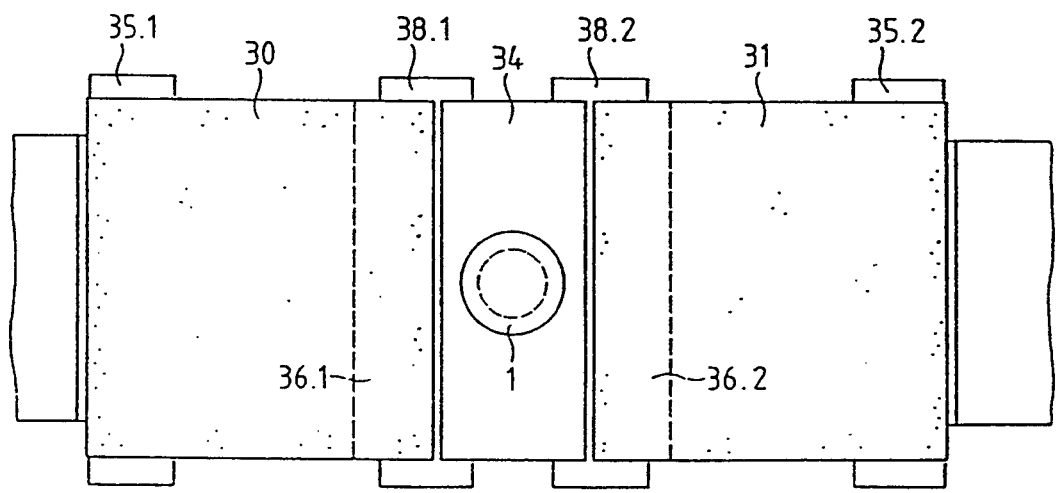

FIG. 3a is a side view and FIG. 3b is a top plan view of FIG. 3a, which depicts an exemplary embodiment of the inventive apparatus suitable for the performance of the inventive method, wherein the through-passing sliver 88, just like in the second variant previously considered with respect to FIG. 1c, is specifically compressed in order to perform the measurement. The apparatus can be incorporated at any suitable processing location for the fibers where the fiber structure, here a sliver 88 is freely transported along a sufficiently long path. Since the sliver 88 must not be braked during its compression, such sliver 88 must be actively transported throughout the measuring path or location 90. In the depicted exemplary embodiment, the sliver 88 is transported in the direction of the arrow B, for example, by the endless revolving belts or transport belts 30, 31 and 32. The upper revolving belts 30 and 31, which here define, infeed and outfeed transport belts 30 and 31, respectively, should be linearly aligned and in the space between such upper revolving belts 30 and 31 there is shown interposed a transparent plate 34 at one side 89 of the sliver 88. The lower endless revolving belt 32 is arranged at the opposite side 91 of the sliver 88, that is at the sliver side facing away from the measuring sensor 1, in such a manner that between the transparent plate 34 and the lower endless revolving belt 32 there is formed the constricted measuring path or location 90. The lower endless revolving belt 32 here simultaneously acts as compression means for the sliver 88.

The measuring sensor or probe 1 is arranged at the side or face of the transparent plate 34 which faces away from the sliver 88. This transparent plate 34, which is stationary, is the only stationary component or part which comes into contact with the throughpassing sliver 88. However, since the sliver 88 is transported at both sides of the transparent plate 34, that is, upstream and downstream thereof, by the revolving belts 30, 31 and 32, the braking action which is present is negligible. Moreover, it is here pointed out that the transparent plate 34 also could be omitted and the measurement then would be accomplished through a suitable gap or opening between the upper endless revolving belts 30 and 31.

Both of these upper endless revolving belts or transport belts 30 and 31 are driven by the drive rolls or rollers 35.1 and 35.2, and at the region neighboring the transparent plate 34 these upper endless revolving belts 30 and 31 are guided about two substantially plate-shaped elements or brackets 36.1 and 36.2, respectively. By virtue of the use of these two plate-shaped elements or brackets 36.1 and 36.2 it is possible, on the one hand, to guide the upper endless revolving belts 30 and 31 near to the region of the transparent plate 34 into the same plane containing such transparent plate 34, and, on the other hand, sufficient space is available at the side of the transparent plate 34 facing away from the through-passing sliver 88 to position the measuring sensor 1 sufficiently close to the transparent plate 34. Similar belt drives are known, for example, from German Published Patent Application No. 3,327,966, published Feb. 21, 1985 which discloses the use of such belt drives in conjunction with a drafting arrangement.

Continuing, the lower endless revolving belt 32 is driven by two drive rolls or rollers 37.1 and 37.2 and guided over two dragged rolls or rollers 38.1 and 38.2. The spacing between these two drive rolls 37.1 and 37.2 and the upper revolving belts 30 and 31 approximately corresponds to the thickness of the sliver 88 which is delivered to the measuring location or site 90. On the other hand, the spacing between the two dragged rolls or rollers 38.1 and 38.2 and the upper revolving belts 30 and 31 is smaller than the first mentioned spacing and approximately corresponds to the degree of compression or compaction of the sliver suitable for performing the color measurement.

In order to ensure that the apparatus does not change in any way the sliver 88, and specifically, does not stretch or brake such sliver 88, it is very important that the belt velocities of the endless revolving belts or transport belts 30, 31 and 32 exactly correspond to the transport velocity of the sliver 88. If this sliver transport velocity is constant, then the velocity of the drive rolls 35.1, 35.2, 37.1 and 37.2 must be correspondingly set. On the other hand, if such sliver transport velocity is not constant, like, for example, at the outlet of a drafting arrangement, the drafting roll velocity of which is regulated by a regulation system as a function of the thickness of the sliver, then the velocities of these drive rolls 35.1, 35.2, 37.1 and 37.2 likewise must be regulated by such regulation system.

Figure 4:
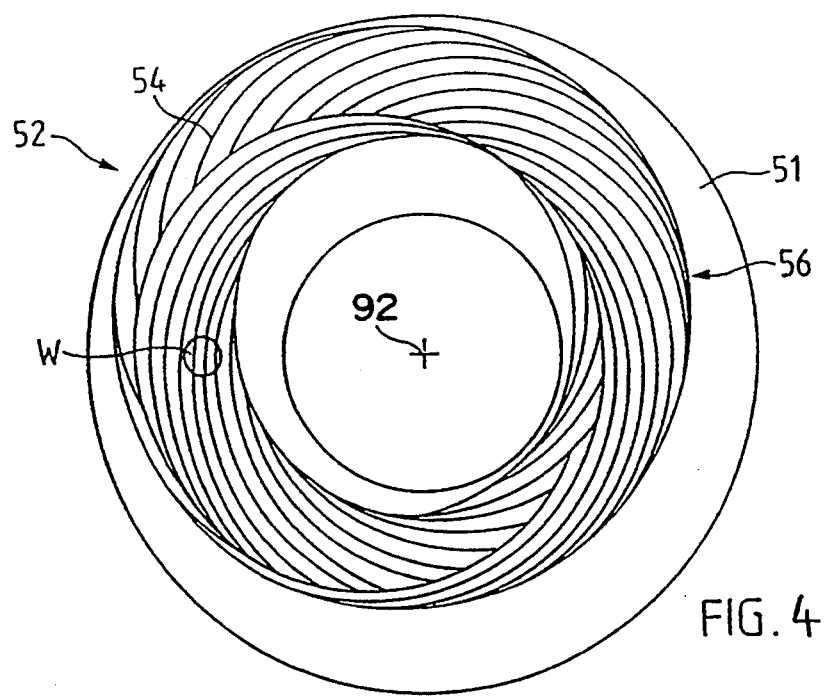
FIG. 4 schematically depicts a further embodiment of the invention in conjunction with a sliver depositing or coiler apparatus for coiling loops or convolutions of sliver into a sliver can.

FIG. 4 schematically depicts another preferred measuring location or site at the region of the sliver deposition apparatus, where a phase of the fiber processing operation, here specifically the sliver processing operation is particularly suitable for the measurement of slivers. At the sliver coiler the sliver is spirally deposited and compressed between the floor of the sliver can and the upper portion of the sliver depositing apparatus in the form of an orderly so-to-speak "sliver cake", also what might be considered as a "sliver tower", which constitutes a predetermined form of the continuous looped deposition of the sliver. The sliver compression occurs due to the fact that a displaceable can or container floor presses the sliver from below against the upper portion of the sliver depositing apparatus, namely, the sliver coiler. During this time, the sliver is continuously infed between the "sliver cake" and the upper portion of the sliver depositing or coiler apparatus. A relative movement takes place between the continually newly formed surface of the "sliver cake" and the upper portion of the sliver depositing or coiler apparatus. The "sliver cake" rotates about the lengthwise axis of the sliver can and during deposition of the sliver there is thus always transported new fiber material past the upper portion of the sliver depositing or coiler apparatus. As a result, there here prevail favorable measuring conditions from the standpoint of the existing fiber processing operation. Therefore, if there is arranged a measuring-auxiliary apparatus, for example, a measuring opening W at the upper portion of the sliver depositing or coiler apparatus through which there is illuminated and through which there can be measured the fiber material pressed from below against the upper portion of the sliver depositing or coiler apparatus, then it is possible to measure the fiber material, which inherently prepares itself for accomplishing the measurement and replenishes itself automatically, without any intervention in or interference with the course of the fiber processing process.

The continually deposited sliver is moved past the measuring sensor or probe, like the measuring sensor 1 of FIG. 1, shortly after deposition in the sliver can and can be measured by such measuring sensor. The measuring window is self-cleaning at the interface with the fiber material, and at the side of the measuring sensor there can be arranged a suitable and thus here not illustrated cleaning and calibration device. As a result, the measuring opening is either continuously freed of dust or the like, in that, for instance, an air jet or air blast moves past the measuring opening, or discontinuously by means of a suitable mechanical cleaning instrument, such as a cleaning brush. The discontinuous mechanical cleaning of the measuring opening, just like the calibration, can be accomplished either off-line and manually or else can be automatically controlled or regulated.

The advantage of such measuring location resides in the fact that the measured fiber material is "non-transparent", that is, the layer thickness and the layer density of the fiber material is so great that background effects are eliminated, and that the fibers of the measured fiber material (after the card or drawframe) are cleaned and ordered (placed in parallelism) and are available in a uniform stored arrangement, as "sliver cakes", so that time-dependent spurious affects do not influence the measurement operation. Care should be taken to ensure that the sliver is not moved past the measuring sensor or probe in the direction of its natural lengthwise orientation, so that there arise brightness fluctuations. This affect can be counter-acted in that there is used an auxiliary sensor arranged upstream of the fiber processing process for determining the sliver density, for example, a capacitive sensor and by means of such there is initiated the color measurement for the measuring operation.

The preferred measuring site or location for the course of the fiber processing process is, as previously stated, at the sliver depositing or coiler apparatus, more specifically, at the upper portion of the sliver depositing or coiler apparatus. In the arrangement of FIG. 4 there is arranged a predetermined observation location, which is correlated to the fiber processing process, for the measured fiber material and which is in the form of the measuring opening W suitable for undertaking a color measurement in the previously proposed manner. Upon the floor or bottom 51 of the depicted sliver can 52 of FIG. 4 there rest the "sliver cake" layers or convolutions 56 of a sliver 54. The eccentric layers or convolutions laid about the center or point of rotation 92 of the sliver can 52, during filling of the sliver into such sliver can 52, are covered by sliver layers or convolutions which are eccentrically shifted in the direction of rotation, resulting in complete covering of the floor 51 of the sliver can 52 even after there have been deposited a few sliver layers or convolutions. As a general rule, this occurs in less than one minute during filling of the sliver can 52. The surface of the "sliver cake" stack then consists of a microscopically complicated arrangement of sliver patterns or courses which, however, when viewed through the measuring opening W, due to the totality of their movement about the center of rotation 92 always depict the same fiber pattern which is conditioned for accomplishing the measurement by virtue of the process-inherent pressing of the "sliver cake" layers against the upper portion of the sliver depositing or coiler apparatus.

Figure 5A:
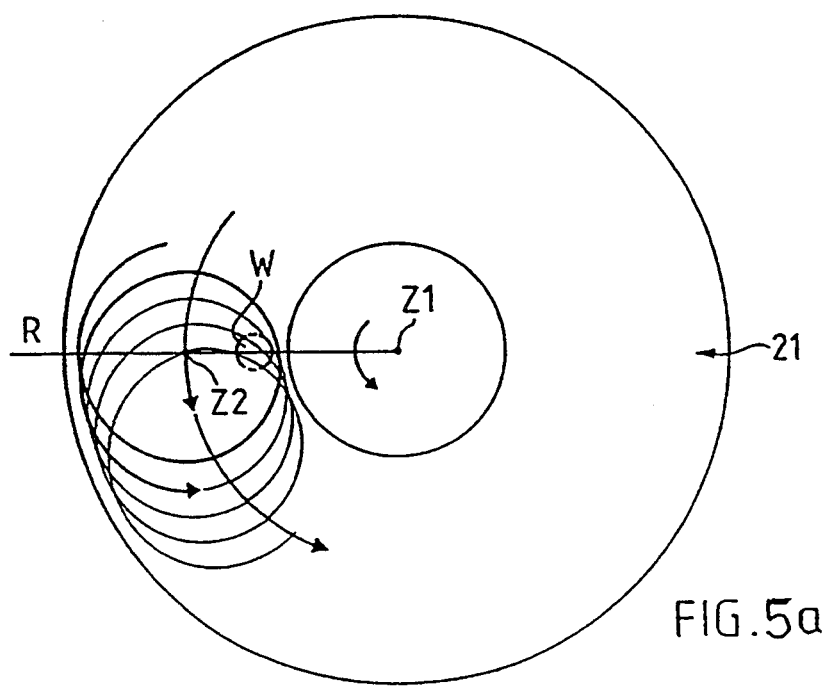
FIG. 5a schematically depicts a still further embodiment of the invention in conjunction with a sliver depositing or coiler apparatus for coiling somewhat differently configured loops or convolutions of sliver into a sliver can.
Figure 5B:
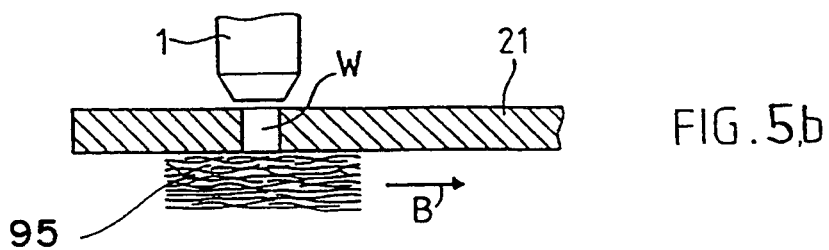

Finally, FIGS. 5a and 5b depict a different manner of depositing the slivers which is inherent to such fiber processing process, wherein the sliver layer coils or convolutions are deposited about a first center of rotation Z1 and a second center of rotation Z2 such that the slivers are spirally arranged about a center. Also here there occurs a pressing or biasing of the slivers, by the action of the upwardly movable, usually spring-loaded can floor, against the upper portion of the sliver depositing or coiler apparatus.

As already depicted in FIG. 4, in the arrangement of FIGS. 5a and 5b the measuring or measurement opening W is arranged at the upper portion of the sliver depositing apparatus 21 against which there is pressed and past which there is moved the uppermost sliver layer, here indicated by reference character 95. As previously explained, the measuring opening W can be closed by a plane glass plate or disk, like the plane glass plate or disk 3a shown in FIG. 1a, or else can be left uncovered or open, in which case, then, the edges of the measuring opening W located at the side of the sliver are appropriately rounded to prevent snagging of the therepast moving sliver. When such measuring opening W is circular in shape, it has a diameter of, for example, about 10 millimeters, so that both possibilities can be resorted to, namely, the minimizing of optical boundary surfaces by omission of a plane glass plate or disk or an enlargement of the measuring opening W which usually requires the use of a plane glass plate or disk or the like. By way of completeness, it is here remarked that it is also possible to use non-planar optical means, such as imaging lenses, as, for instance, disclosed in the commonly assigned, copending United States application Ser. No. 07/668,030, Mar. 12, 1991, and entitled "Method and Apparatus For Measuring the Natural Color of Slivers", to which reference may be readily had and the disclosure of which is incorporated in its entirety herein by reference.

In a direction radially of the rotational axis of the sliver can, the position of the measuring opening can be selected such that there is present the finest structure of the compressed fiber material moving past and beneath the measuring opening, which, as a rule, is the case at the inner edge of the compressed "sliver cake". The position of the measuring locations or sites can be thus optimized.

During normal operation, color values of the sliver are measured at time intervals of about, for example, 10 seconds. The sliver can exchange operation needed each time the sliver can is full with sliver interrupts the color measurements during about 10% to 15% of the time needed for filling of a can. This constitutes a so-to-speak blind or ineffectual phase of the measuring operation, in other words, constitutes a gap or interruption in the measurement procedure. This measuring gap or interruption, during which there can not be obtained any color measurement data, can be reduced and even eliminated by employing further color measuring sensors or probes at further sliver depositing or coiler apparatuses or installations of parallel operating cards processing the same type of fibers. If the sliver can exchange operation is organized in time such that during the exchange of a sliver can there is always obtained color data from at least one of the measuring sensors, then it is possible to measure quasi-continuously the color of the fiber material. As a practical matter the situation does not normally occur that all sliver cans are simultaneously exchanged, particularly then if there are also implemented organizational measures regarding the exact point in time when the sliver cans are exchanged.

Through the use of a second measuring sensor at a neighboring sliver depositing apparatus the sliver can exchange operation does not constitute a disturbing factor in the overall timewise monitoring of the fiber structures to be investigated. As stated, the probability is real slight that both sliver depositing or coiler apparatuses will undergo a sliver can exchange operation at the same time. Moreover, the use of a second measuring location or site, or even further ones, affords additional advantages, namely, that of redundancy due to the accomplishment of twice as many measurements if such measurements are simultaneously carried out (the redundancy only then fails to exist during the very brief time when there is accomplished a sliver can exchange operation):

The signals obtained during the measurement of the aforementioned concentration of different types of fibers in the investigated fiber structure, namely the fiber composite or the fiber sliver, can be evaluated in a suitable evaluation device or control, so that there is displayed at a monitor either the proportion of, for example, synthetic fibers in the entire fiber structure, or else in a control or regulator means, as described in the aforementioned commonly assigned European Published Patent Application No. 0,362,538, published Apr. 11, 1990 and its cognate U.S. Pat. No. 5,025,533, granted Jun. 25, 1991, for affecting the blending of the fiber constituents.

As a last point there are enumerated different advantages of the prior discussed redundancy:

(i) mutual checking of the measuring sensors by comparison of the derived measuring signals; and (ii) determination of possibly occurring de-blending phenomenon in the card filling chute or duct and in the card itself.

While there are shown and described present preferred embodiments of the invention, it is distinctly to be understood the invention is not limited thereto, but may be otherwise variously embodied and practiced within the scope of the following claims.

What is claimed is:

1. A method for determining, during continuous operation of a textile fiber processing apparatus, a characteristic in a fiber structure composed of different individual types of textile fibers, said method comprising the steps of:

selecting a pregiven blending proportion of said individual types of textile fibers in said fiber structure as a characteristic to be determined; and measuring a concentration of at least one of said individual pregiven different types of textile fibers for determining said blending proportion.

2. The method according to claim 1, further including the step of:

employing as the fiber structure a moving fiber composite; and measuring the concentration of the individual pregiven types of fibers in the moving fiber composite.

3. The method according to claim 1, further including the step of:

employing as the fiber structure a moving sliver; and measuring the concentration of the individual pregiven types of fibers in the moving sliver.

4. The method according to claim 1, wherein said fiber structure comprises a fiber composite and wherein said step of measuring a concentration of at least one of said individual pregiven different types of fibers comprises measuring a concentration of at least one of said individual pregiven different types of fibers of said fiber composite during movement of said fiber composite, said method further including the step of:

performing the measurement of the concentration of the individual pregiven types of fibers in the moving fiber composite, by evaluation of spectrums in near infrared range.

5. The method according to claim 4, further including the steps of:

exposing the fiber structure to a fiber processing process;

compacting the fiber structure at a measuring location containing a light passage arranged such that there is not affected the fiber processing process during such time that the fiber structure is exposed to the fiber processing process;

performing the measurement of the concentration of the individual pregiven types of fibers in the fiber composite, by illuminating the fiber structure with light transmitted through the light passage at the measuring location where the fiber structure is compacted;

receiving light reflected back from a fiber structure in a direction substantially perpendicular to the lengthwise axis of the fiber structure; and evaluating the received light.

6. The method according to claim 5, wherein:
the step of compacting the fiber structure at the measuring location is accomplished by gathering the fiber structure at the measuring location.

7. The method according to claim 5, wherein:
the step of compacting the fiber structure at the measuring location is accomplished by compressing the fiber structure at the measuring location.

8. The method according to claim 5, further including the step of:
selecting as the measuring location a location where the fiber structure is deposited in overlapping layers.

9. The method according to claim 1, wherein:
the step of measuring a concentration of at least one of said individual pregiven different types of fibers comprises the steps of:
transmitting light to said fiber structure;
receiving light reflected from said fiber structure; and
analyzing said reflected light.

10. The method according to claim 9, wherein:
said steps of transmitting and receiving light comprises transmitting and receiving at least infrared light.

11. In a method of blending textile fibers of different fiber origin in the formation of an entire fiber mixture, wherein each fiber origin possesses pregiven fiber characteristics and in which each fiber origin constitutes a mixing component of a predetermined percentual proportion, and wherein the entire fiber mixture possesses predetermined fiber characteristics, and the mixing components constitute variable components which can be controlled at all times, and the percentual proportion of each component, in order to attain such predetermined fiber characteristics of the entire fiber mixture, is automatically optimized while taking into account the fiber characteristics of the individual components, and the component mixture is determined as a function of pregiven and determined characteristics of a product which is subsequently fabricated, including an intermediate product or a final product, and upon deviation from such pregiven and determined characteristics of the product such deviations are immediately and automatically corrected, the improvement which comprises the steps of:
selecting as the characteristic of a fiber structure which is to be determined and defining the product, the concentration of individual pregiven types of fibers in the fiber structure;
measuring a concentration of the individual pregiven types of fibers in the fiber structure.

12. The method according to claim 11, wherein:
the intermediate product is a card sliver.

13. The method according to claim 11, wherein:
the final product is a yarn.

14. The method according to claim 11, further including the step of:
performing the measurement of the concentration of the individual pregiven types of fibers in the fiber structure, by evaluation of spectrums in near infrared range.

15. The method according to claim 11, further including the step of:
performing the measurement of the concentration of the individual pregiven types of fibers in the fiber structure, by evaluation of spectrums in near infrared range.

16. The method according to claim 15, further including the steps of:
exposing the fiber structure to a fiber processing process;
compacting the fiber structure at a measuring location containing a light passage arranged such that there is not affected the fiber processing process during such time that the fiber structure is exposed to the fiber processing process;
performing the measurement of the concentration of the individual pregiven types of fibers in the fiber composite, by illuminating a fiber structure with light transmitted through the light passage at the measuring location where the fiber structure is compacted;
receiving light reflected back from the fiber structure in a direction substantially perpendicular to the lengthwise axis of the fiber structure; and
evaluating the received light.

17. The method according to claim 16, wherein:
the step of compacting the fiber structure at the measuring location is accomplished by gathering the fiber structure at the measuring location.

18. The method according to claim 16, wherein:
the step of compacting the fiber structure at the measuring location is accomplished by compressing the fiber structure at the measuring location.

19. The method according to claim 16, further including the step of:
selecting as the measuring location a location where the fiber structure is deposited in overlapping layers.

20. An apparatus for determining a characteristic of a fiber structure constituting the blending proportion of individual pregiven types of fibers in the entire fiber structure, comprising:
means for processing fibers in accordance with a fiber process for producing the fiber structure;
means for compacting the fiber structure at a measuring location containing a light passage arranged such that there is not affected the fiber processing process during such time that the fiber structure is exposed to the fiber processing process;
means for measuring the concentration of the individual pregiven types of fibers in the fiber structure after the fibers are processed into the fiber structure, by illuminating the fiber structure with light transmitted through the light passage at the measuring location where the fiber structure is compacted;
said measuring means receiving light reflected back from the fiber structure in a direction substantially perpendicular to a lengthwise axis of the fiber structure; and
said measuring means including means for evaluating the received light.

21. The apparatus according to claim 20, wherein: the measuring means comprise spectrometer means.

22. The apparatus according to claim 21, wherein:
the spectrometer means comprises a measuring instrument having a light wave guide and a measuring head, and an evaluation unit having a data screen, which evaluates spectra in the near infrared range.

23. The apparatus according to claim 20, wherein:
the means for compacting the fiber structure at the measuring location comprises a sliver funnel;
said sliver funnel including an opening defining a measuring opening, and a funnel neck;
said measuring opening possessing a substantially flat rectangular cross-sectional configuration;
said measuring means comprising a measuring sensor positioned substantially perpendicular to the funnel neck and aligned with the measuring opening; and
said sliver funnel containing a transparent wall confronting the measuring sensor.

24. The apparatus according to claim 20, wherein:
the means for compacting the fiber structure at the measuring location comprises at least one respective transport belt arranged to opposite sides of the fiber structure which constitutes a moving fiber structure;
a transparent plate arranged at one side of the moving fiber structure;
said measuring means comprises a measuring sensor arranged at a side of the transparent plate facing away from the moving fiber structure; and
the transport belts and the transparent plate being arranged such that, as viewed in a predetermined direction of travel of the moving fiber structure, the spacing between at least one of the transport belts and the transparent plate successively decreases in the direction of the transparent plate and assumes a minimum value at the region of the transparent plate.

25. The apparatus according to claim 24, wherein:
the at least one respective transport belt arranged to opposite sides of the moving fiber structure comprises two transport belts arranged at a side of the moving fiber structure which confronts the measuring sensor and a further transport belt arranged at a side of the moving fiber structure which faces away from the measuring sensor;
the transparent plate being arranged between the two transport belts arranged at the side of the moving fiber structure which confronts the measuring sensor and respectively defining an infeed transport belt and an outfeed transport belt; and
substantially plate-shaped brackets for guiding the infeed transport belt and the outfeed transport belt to the immediate region of the transparent plate.

* * * * *